United States Patent [19]

Berner et al.

[11] 4,428,953
[45] Jan. 31, 1984

[54] PLEUROMUTILIN DERIVATIVES, THEIR PRODUCTION AND USE

[75] Inventors: Heinz Berner, Vienna; Friederike Turnowsky, Maria Enzersdorf; Georg Laber, Vienna; Johannes Hildebrandt, Oeynhausen, all of Austria

[73] Assignee: Sandoz, Ltd., Basel, Switzerland

[21] Appl. No.: 356,043

[22] Filed: Mar. 8, 1982

Related U.S. Application Data

[63] Continuation of Ser. No. 198,292, Oct. 20, 1980, abandoned, which is a continuation-in-part of Ser. No. 111,446, Jan. 11, 1980, abandoned.

[30] Foreign Application Priority Data

Jan. 12, 1979 [CH] Switzerland .................. 309/79
Aug. 8, 1979 [CH] Switzerland ................ 7274/79

[51] Int. Cl.³ .................. A01N 43/64; C07D 249/12; C07D 249/14; C07D 401/04
[52] U.S. Cl. .................. 424/263; 424/250; 424/251; 424/269; 424/270; 424/273 R; 424/273 B; 544/238; 544/239; 544/240; 544/241; 544/249; 544/318; 544/319; 544/366; 546/276; 546/285; 548/141; 548/160; 548/187; 548/265; 548/266; 548/267; 548/268; 548/329; 548/330; 548/337; 548/528
[58] Field of Search .............. 548/266, 265, 267, 268; 424/269, 250, 263; 546/285, 276; 544/366

[56] References Cited

U.S. PATENT DOCUMENTS 3,919,290 11/1975 Egger et al. ................ 424/269
3,979,423 11/1976 Riedl ................ 546/285
4,113,943 9/1978 Treuner et al. ................ 424/246
4,143,166 3/1979 Takaya et al. ................ 424/246
4,160,086 7/1979 Burton et al. ................ 424/246

Primary Examiner—Alton D. Rollins
Attorney, Agent, or Firm—Gerald D. Sharkin; Robert S. Honor; Thomas O. McGovern

[57] ABSTRACT

Novel pleuromutilin derivatives of formula I,

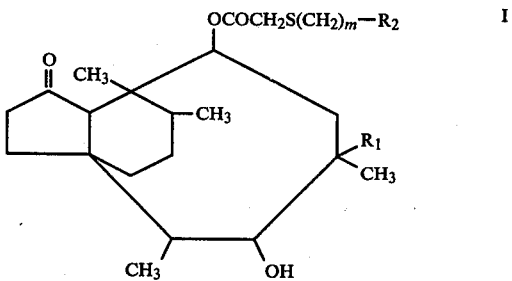

in which
$R_1$ is ethyl or vinyl,
m is 0 or 1, and
$R_2$ is a heterocyclic radical, in which a 5- or 6-membered, unsaturated or saturated heterocyclic ring containing one or more hetero atoms selected from oxygen, sulphur and nitrogen, is attached to the $-S(CH_2)_m-$ group,
provided that when m is 0, $R_2$ is other than pyridyl,
their production and use as antimicrobial agents are described.

18 Claims, No Drawings

PLEUROMUTILIN DERIVATIVES, THEIR PRODUCTION AND USE

This is a continuation of application Ser. No. 198,292 filed Oct. 20, 1980, now abandoned which in turn is a continuation-in-part of Ser. No. 111,446, filed Jan. 11, 1980, now abandoned.

This invention provides compounds of formula I,

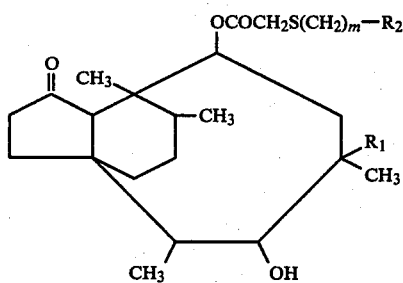

I in which
$R_1$ is ethyl or vinyl,
m is 0 or 1, and
$R_2$ is a heterocyclic radical, in which a 5- or 6-membered, unsaturated or saturated heterocyclic ring containing one or more hetero atoms selected from oxygen, sulphur and nitrogen, is attached to the $-S(CH_2)_m-$ group,
provided that when m is 0, $R_2$ is other than pyridyl.

The invention also provides a process for the production of compounds of formula I, characterised by reacting a compound of formula II,

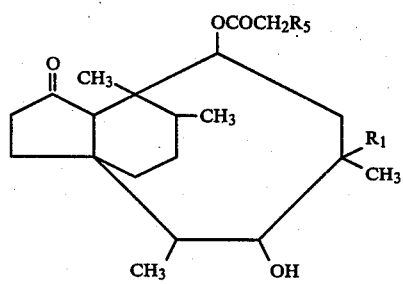

II in which
$R_1$ is as defined above, and
$R_5$ is chlorine, bromine or $-OSO_2R_7$, in which $R_7$ is alkyl or aryl,
with a compound of formula III,

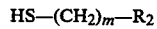

HS—(CH$_2$)$_m$—R$_2$     III in which m and $R_2$ are as defined above.

The process is suitably carried out in the presence of an alkali metal lower alkoxide, for example sodium ethoxide or methoxide. This is preferably produced in situ. Conveniently, the compound of formula III may be dissolved in a solution of sodium in a water-free lower alkanol, e.g. methanol or ethanol. A solution of the compound of formula II in an inert organic solvent, e.g. an aliphatic ketone, such as methyl ethyl ketone or acetone, is then conveniently added. The process is suitably effected at a temperature from room temperature to the reflux temperature of the reaction mixture, in particular from 22° to 55° C. The reaction time may typically vary from 2 to 12 hours.

The resulting compounds of formula I may be isolated and purified using conventional techniques. Where required, free base forms thereof may be converted into salt forms, in particular into acid addition salt and quaternary ammonium salt forms, in conventional manner, and vice versa.

$R_2$ suitably signifies a 5- or 6-membered saturated or unsaturated heterocyclic ring containing one or more hetero atoms selected from oxygen, sulphur and nitrogen. The heterocyclic ring is preferably a 5-membered saturated or unsaturated ring containing one or more hetero atoms selected from nitrogen and sulphur. The ring may be unsubstituted. Alternatively, it may be mono- or poly-substituted. Suitable substituents include mercapto, thioxo, hydroxy, lower alkyl, lower alkanoyl, lower sulfoxyl, nitro, lower alkylsulphonyl, trifluoromethyl, formyl, lower alkoxycarbonyl, lower hydroxyalkyl, lower dihydroxyalkyl and halogen.

Further suitable substituents are of formula IV, IVa and IVb

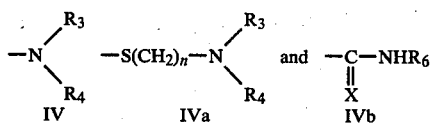

in which
either $R_3$ and $R_4$ are the same or different and each is hydrogen, lower hydroxyalkyl, lower dihydroxyalkyl, unsubstituted or substituted (for example by lower alkoxysulphonyl) lower alkanoyl, lower alkyl sulphonyl or lower alkyl,
or $R_3$ and $R_4$ together with the nitrogen atom form a piperazinyl radical, which may be substituted on the second nitrogen atom by lower alkyl, lower hydroxyalkyl or lower dihydroxyalkyl,
n is 2 to 5,
X is oxygen or sulphur, and
$R_6$ is lower alkyl or lower alkoxycarbonyl.

Other substituents include further 5- or 6-membered, saturated or unsaturated heterocyclic rings, e.g. pyridyl, which may themselves be unsubstituted or mono- or poly-substituted as described above.

Finally, the heterocyclic ring of $R_2$ may suitably be fused to one or more 5- or 6-membered, saturated or unsaturated carbocyclic or heterocyclic, preferably carbocyclic, e.g. benzene, rings. This ring may also be unsubstituted or similarly mono- or poly-substituted, as described above.

$R_3$ and $R_4$ are preferably hydrogen, lower alkanoyl, or methylsulphonyl.

The preferred substituents on the heterocyclic ring of $R_2$ include lower alkylsulphonyl, lower alkyl, lower alkoxy carbonyl, trifluoromethyl, formyl, a radical of formula IV in which $R_3$ and $R_4$ are the same or different and are hydrogen, lower alkanoyl, or methylsulphonyl, a radical of formula IVb or a 6-membered saturated or unsaturated heterocyclic ring.

As used herein, the term "lower" signifies preferably 1 to 4, more preferably 1 to 2 carbon atoms. "Halogen" signifies chlorine, bromine, fluorine or iodine, preferably chlorine, bromine or fluorine, more preferably chlorine.

The preferred heterocyclic rings in $R_2$ linked to the $-S(CH_2)_m-$ radical contain one or more hetero atoms selected from nitrogen and sulphur. The more preferred ring contains at least one nitrogen atom.

One group of such hetero rings may contain nitrogen as the sole hetero atom, in particular 1, 2 or 3 nitrogen hetero atoms. Suitable 5- or 6-membered hetero rings containing a single nitrogen atom include pyridine (when m is 1), pyrrole and 4,5-dihydro-3H-pyrrole. Suitable 5- or 6-membered rings containing 2 nitrogen atoms include imidazole, pyridazine, pyrimidine. Such rings may be fused to, e.g. one or more benzene rings, e.g. to form benzimidazole or perimidine. Suitable 5- or 6-membered hetero rings containing 3 nitrogen atoms include 1,2,4-triazole.

Another group of hetero rings may contain 1 nitrogen atom and 1 sulphur atom, e.g. thiazole, 4,5-dihydrothiazole and benzothiazole. Another group of hetero rings contain 2 nitrogen and 1 sulphur atom, e.g. 1,3,4-thiadiazole.

Preferred compounds are those in which the heterocyclic ring of $R_2$ is bound to the —S—$(CH_2)_m$— group via a ring carbon atom. Particularly preferred compounds are those in which the hetero ring of $R_2$ is 1,2,4-triazole.

A particularly preferred group of compounds are those in which $R_2$ is formula V,

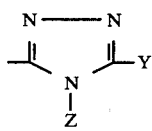

in which
Z is hydrogen, lower alkylsulphonyl, amino a group of formula IV, IVa or IVb; formyl, and
Y is hydrogen, amino, trifluoromethyl, lower alkyl, a group of formula IV, or pyridyl.

More preferably Z is hydrogen, lower alkylsulphonyl, a group of formula IV in which $R_3$ and $R_4$ are the same or different and are hydrogen, lower alkanoyl or methylsulphonyl, a group of formula IVb or pyridyl. Y is hydrogen, trifluoromethyl, lower alkyl, pyridyl or a group of formula IV in which $R_3$ and $R_4$ are the same or different, and are hydrogen, lower alkanoyl or methylsulphonyl.

The compounds of formula I are useful as chemotherapeutic agents, in particular as antimicrobial agents, as indicated for example by their inhibiting effect against various bacterial strains, e.g. *Staph. aureus, Staph. epidermis, Strept. pyogenes, Strept. aronson, Strept. pneumoniae, Strept. faecalis, Strept. viridans, Corynebact. pyogenes, Sarcina lutea, Klebsiella pneumoniae,* and *Haemophilus influenzae,* in vitro in the serial broth dilution test at concentrations, for example, of 0.01 to 25 μg/ml, and in in vivo tests in mice. The compounds also show an inhibiting effect against various mycoplasma, e.g. *M. hominis, M. arthritidis, M. pneumoniae,* and *Ureaplasma urealyticum,* and *chlamydia,* in vitro in the serial broth dilution test at concentrations of, for example, 0.008 to 2.5 μg/ml.

The compounds also show an inhibiting effect against various obligatory anaerobes, e.g. *Bacteroides fragilis, Bacteroides melaninogenicus, Sphaerophorus necrophorus, Clostridium perfringens,* etc., in vitro in the serial broth dilution test at concentrations of for example 0.1 to 4 μg/ml, and in vivo in mice at a dosage of for example 50 to 200 mg/kg of animal body weight, p.o. or s.c.

The compounds are therefore useful as antimicrobial agents, in particular as antibacterially active antibiotics and for treatment of infections caused by obligatory anaerobes.

For the above-mentioned uses, the effective dosage will of course vary depending on the particular compound employed, the mode of administration and the treatment desired. However, in general, satisfactory results can be obtained when the compounds are administered at a daily dosage of from about 10 to 300 mg/kg of animal body weight, suitably given in divided doses two to four times daily. For most larger mammals, the total daily dosage is from about 1 to 3 g and dosage forms suitable for internal administration comprise about 250 to 1500 mg of the compound in admixture with a solid or liquid pharmaceutical carrier or diluent.

The compounds alone or in admixture with a tetracyclin, may be administered orally or parenterally in such forms as tablets, capsules, powders, granulates, and injectable or infusion preparations, e.g. solutions or suspensions. The compounds may also be employed in the form of creams or tinctures. For veterinary purposes, the compounds may also be administered as food or drink additives.

It has also been found that mixtures of the compounds of formula I with a tetracyclin show a synergistic antibacterial effect against strains with R-factor coded tetracyclin resistence. This is indicated for example by the determination of the minimal inhibitory concentrations of the mixture and the individual components in the serial broth dilution test, and by evaluating the results by the method of Löwe (isobole diagram), Die Antibiotika, Volume 1, part 1, 65ff, 1962. Conventional tetracyclines, e.g. chlorotetracyclin, oxytetracyclin, demethyltetracyclin, tetracyclin dioxycyclin, monocyclin, metacyclin, and rolitetracyclin, may be employed in such mixtures. The quantity of the compound of formula I in such mixtures is suitably 10 to 90%, preferably 20 to 35%, in particular 25%, while the quantity of the tetracyclin is suitably from 90 to 10%, preferably 80 to 65%, particularly 75% (these percentages being by weight).

The mixtures are particularly useful in treating infections of the gastrointestinal tract and other local infections of the organism.

The compounds of formula I, when used alone or in admixture with a tetracyclin, may be employed in free base form or in the form of chemotherapeutically acceptable acid addition or quaternary ammonium salts. These salt forms have the same order of activity as the free base forms.

Suitable acid addition salt forms include the hydrochloride, hydrogen fumarate, fumarate and naphthalene-1,5-sulphonate.

The compounds (or mixtures thereof with a tetracycline) may be admixed with a chemotherapeutically acceptable diluent or carrier and, optionally other conventional excipients for the production of galenic forms. Suitable excipients include sweeteners, aromas, colouring agents, preserving agents, e.g. ethyl-o-hydroxybenzoate, fillers or carriers, e.g. diluents, such as calcium carbonate, disintegrating agents, e.g. starch or alginic acid, binding agents, e.g. starch, gelatine or acacia, and lubricating agents, e.g. magnesium stearate, stearic acid or talc. Oral liquid forms may contain conventional suspending agents, e.g. methylcellulose, tragacanth or sodium alginate. Suitable wetting agents include lecithin, polyoxyethane stearate and polyoxyethylene sorbitan monooleate. For the production of capsules, suitable diluents include calcium carbonate, calcium phosphate and kaolin.

The preferred compound of formula I is that of Example 1, hereinafter.

The following Examples illustrate the invention. All temperatures are in degrees Centigrade.

EXAMPLE 1

19,20-Dihydro-14-O-[(3-amino-1,2,4-triazole-5-yl)thioacetyl]mutilin 2.3 g of sodium are taken up in 500 ml of absolute ethanol. After formation of the sodium ethoxide, 11.6 g of 3-amino-5-mercapto-1,2,4-triazole are added to the solution.

The mixture is allowed to react for 3 hours at 25° and is then mixed with a solution of 53.5 g of 19,20-dihydro-22-O-tosyl-pleuromutilin in 200 ml of ethylmethylketone. The homogenous reaction mixture is held for 12 hours at 25° and then poured onto water and extracted 3 times with 500 ml of ethyl acetate. The purified ethyl acetate extract is shaken with water, dried over $Na_2SO_4$ and evaporated in vacuo. The crude product is chromatographed over silica gel (eluant: ethyl acetate) to obtain the heading compound, m.p. 213°–215° (isopropanol/$H_2O$).

NMR (DMSO): 5.76 (broad, 2H, $NH_2$); 5.52 (d, 1H, $H_{14}$, $J_{H14H13}=8$ Hz); 3.76 (s, 2H, S—$CH_2$—CO); 3.35 (m, 1H, $H_{11}$).

IR (—KBr): 2600–3600 (broad), 1720, 1635, 1280 cm$^{-1}$.

The compounds of the following Examples may be produced in manner analogous to that of Example 1, using appropriate starting materials in approximately equivalent amounts.

EXAMPLE 2

14-O-[3-Amino-1,2,4-triazol-5-yl)thioacetyl]mutilin

NMR (CDCl$_3$): 5.68 (d, 1H, $H_{14}$, $J_{H14H13}=8$ Hz); 3.34 (d, 1H, $H_{11}$, $J_{H11H10}=6$ Hz); 3.7 (s, 2H, S—$CH_2$—CO); 5.26–4.95 (m, 4H, $NH_2+2H_{20}$); 6.5–6.16 (m, 1H, $H_{19}$).

IR (KBr): 3300 (broad), 1720, 1625, 1575, 1270 cm$^{-1}$.

EXAMPLE 3

14-O-[(Imidazole-2-yl)thioacetyl]mutilin

NMR (CDCl$_3$/DMSO 5:1): 6.09 (s, 2H, Imidazol H); 5.65 (d, 1H, $H_{14}$, $J_{H14H13}=8$ Hz); 3.76 (s, 2H, S—$CH_2$CO); 3.4–3.2 (m, 1H, $H_{11}$).

IR (KBr): 3600–2600 (broad), 1730, 1705, 1270 cm$^{-1}$.

EXAMPLE 4

14-O-[(Perimidine-2-yl)thioacetyl]mutilin

NMR (CDCl$_3$): 7.0–7.2 (m, 4H, arom. H); 5.74 (d, 1H, $H_{14}$, $J_{H14H13}=8$ Hz); 3.72 (AB-System, 2H, S—$CH_2$—CO, $J=16.2$ Hz); 3.42–3.22 (m, 1H, $H_{11}$).

IR (KBr): 3600–3100 (broad), 1720, 1625, 1585, 1270, 820, 770 cm$^{-1}$.

EXAMPLE 5

14-O-[(4,5-Dihydro-3H-pyrrole-2yl)thioacetyl]mutilin

NMR (CDCl$_3$): 5.74 (d, 1H, $H_{14}$, $J_{H14H13}=8$ Hz); 3.96–3.58 (m, 4H, 2-Pyrrolidin H+S—$CH_2$—CO); 3.36 (dd, 1H, $H_{11}$, $J=6.3$ Hz, $J=10.8$ Hz).

IR (CHCl$_3$): 1720, 1590 cm$^{-1}$.

EXAMPLE 6

14-O-[(Benzimidazole-2-yl)thioacetyl]mutilin

NMR (CDCl$_3$): 7.5–7.0 (m, 4H, arom. H); 5.64 (d, 1H, $H_{14}$, $J_{H14H13}=8.2$ Hz); 4.1 (s, 2H, S—$CH_2$—CO); 3.38 (d, 1H, $H_{11}$, $J_{H11H10}=6.3$ Hz).

IR (KBr): 3550–2600 (breit), 1720, 1270, 740 cm$^{-1}$.

EXAMPLE 7

14-O-[(4-Methylsulfonyl-5-amino-1,2,4-triazole-3-yl)thioacetyl]mutilin

NMR (CDCl$_3$): 5.9 (s, 2H, $NH_2$); 5.76 (d, 1H, $H_{14}$, $J_{H14H13}=8$ Hz); 3.81 (s, 2H, S—$CH_2$—CO); 3.3 (s, 3H, $CH_3SO_2$—); 3.4 (m, 1H, $H_{11}$).

IR (KBr): 3400 (broad), 1720, 1625, 1265, 1275, 1180 cm$^{-1}$.

EXAMPLE 8

14-O-[(3-Mercaptopyridazine-6-yl)thioacetyl]-19,20-dihydromutilin

NMR (CDCl$_3$): 7.5 (d, 1H, arom. H, $J=9$ Hz); 6.9 (d, 1H, arom. H, $J=9$ Hz); 5.64 (d, 1H, $H_{14}$, $J_{H14H13}=8$ Hz); 3.79 (s, 2H, S—$CH_2$—CO); 3.44 (d, 1H, $H_{11}$, $J_{H11H10}=6$ Hz).

IR (KBr): 3400 (broad), 1720, 1270, 1155, 1140 cm$^{-1}$.

EXAMPLE 9

14-O-[(2-Isopropyl-4-hydroxypyrimidine-6-yl)methylthioacetyl]mutilin

NMR (CDCl$_3$): 6.32 (s, 1H, arom. H); 5.81 (d, 1H, $H_{14}$, $J_{H14H13}=8$ Hz); 3.62 (s, 2H, S—$CH_2$—CO); 3.3 (s, 2H, S—$CH_2$—Arom.); 3.4 (m, 1H, $H_{11}$).

IR (KBr): 3400 (broad), 1720, 1650, 1590, 1275 cm$^{-1}$.

EXAMPLE 10

14-O-{[3-(4-Hydroxyethylpiperazine-1-yl-äthylthio)-pyridazin-6-yl]thioacetyl}mutilin hydrochloride form NMR (CDCl$_3$/CD$_3$OD 50:1): 7.26 (s, 2H, arom. H); 5.7 (d, 1H, $H_{14}$, $J_{H14H13}=8$ Hz).

IR (KBr): 3350 (broad), 1720, 1380, 1270, 1140 cm$^{-1}$.

EXAMPLE 11

14-O-[(6-Nitrobenzothiazol-2-yl)thioacetyl]mutilin

NMR (CDCl$_3$): 8.68 (d, 1H, arom. H, $J=2.3$ Hz); 8.3 (dd, 1H, arom.H, $J_1=2.3$ Hz, $J_2=9$ Hz); 7.84 (d, 1H, arom. H, $J=9$ Hz); 5.78 (d, 1H, $H_{14}$, $J_{H14H13}=8$ Hz); AB-System: ($v_A=3.18$, $v_B=3.06$, S—$CH_2$—CO, $J=16.2$ Hz); 3.34 (dd, 1H, $H_{11}$, $J=6$ Hz, $J=10.8$ Hz).

IR (KBr): 3400 (broad), 1720, 1510, 1325, 1265, 1010 cm$^{-1}$.

EXAMPLE 12

14-O-[(4-Methyl-6-hydroxypyrimidin-2-yl)-thioacetyl]-mutilin

NMR (DMSO): 5.94 (s, 1H, arom. H); 5.53 (d, 1H, $H_{14}$, $J_{H14H13}=8$ Hz); 3.9 (s, 2H, S-$CH_2$CO); 3.4 (m, 1H, $H_{11}$); 2.14 (s, 3H, $CH_3$).

IR (KBr): 3400 (broad), 1720, 1650, 1525, 1270, 1160 cm$^{-1}$.

EXAMPLE 13

14-O-[(4-Ethoxycarbonyl-3,5-dimethylpyrrol-2-yl)thioacetyl]mutilin

NMR (CDCl$_3$): 8.75 (b, 1H, NH); 5.74 (d, 1H, H$_{14}$, J$_{H14H13}$=8 Hz); 4.26 (q, 2H, —OCH$_2$CH$_3$); 3.22 (s, 2H, S-CH$_2$CO); 3.36 (dd, 1H, H$_{11}$, J=6.3 Hz, J=10.8 Hz); 2.46 (s, 3H, CH$_3$-Pyrrol); 2.28 (s, 3H, CH$_3$—Pyrrol).

IR (KBr): 3600–3200 (broad), 1720, 1780, 1250, 1100 cm$^{-1}$.

EXAMPLE 14

14-O-[(1-Methylimidazol-2-yl)thioacetyl]mutilin

NMR (CDCl$_3$): 7.0 (d, 1H, Imidazole H, J=1.8 Hz), 6.86 (d, 1H, Imidazole H, J=1.8 Hz); 5.7 (d, 1H, H$_{14}$, J$_{H14H13}$=8 Hz); 3.78 (s, 2H, S-CH$_2$CO); 3.62 (s, 3H, N-CH$_3$); 3.34 (m, 1H, H$_{11}$).

IR (KBr): 3200 (broad), 1720, 1270 cm$^{-1}$.

m.p.: 135°–136°.

EXAMPLE 15

14-O-[(3-Mercaptopyridazin-6-yl)thioacetyl]mutilin

NMR (CDCl$_3$): AB-System of the Pyridazineprotons ($v_A$=7.5, $v_B$=6.9, J$_{AB}$=9 Hz); 5.64 (1H, H$_{14}$, J$_{H14H13}$=7 Hz); 3.78 (s, 2H, S-CH$_2$-CO); 3.44 (1H, H$_{11}$, J$_{H11H10}$=6.3 Hz).

IR (KBr): 3400 broad (OH), 1725 (CO), 1140, 1155 cm$^{-1}$.

EXAMPLE 16

14-O-[(3-Chlorpyridazin-6-yl)thioacetyl]mutilin

NMR (CDCl$_3$): 5.78 (d, 1H, H$_{14}$, J$_{H14H13}$=8 Hz); 3.38 (m, 1H, H$_{11}$); 1.44 (s, 3H, (CH$_3$)$_{15}$); 1.21 (s, 3H, (CH$_3$)$_{18}$); AB-System of the Pyridazin-H ($v_A$=7.29, $v_B$=7.33, J$_{AB}$=9 Hz); AB-System (CH$_2$)$_{22}$-($v_A$=4.12, $v_B$=4.02, J$_{AB}$=16 Hz).

IR (KBr): 3500 (OH), 1720 (CO) cm$^{-1}$.

EXAMPLE 17

14-O-[(4,5-Dihydrothiazol-2-yl)thioacetyl]mutilin

NMR (CDCl$_3$): 5.75 (d, 1H, H$_{14}$, J$_{H14H13}$=8 Hz); 3.81 (s, 2H, -(CH$_2$)$_{22}$-); 1.46 (s, 3H, (CH$_3$)$_{15}$); 1.17 (s, 3H, (CH$_3$)$_{18}$); 4.14 (t, 2H, -S-CH$_2$, J=8 Hz); 3.4 (t, 2H, =N-CH$_2$).

IR (KBr): 3500 (OH), 1710 (CO), 1570 cm$^{-1}$.

EXAMPLE 18

14-O-[(3-Diethylaminoethylthiopyridazin-6-yl)thioacetyl]mutilin hydrogen fumarate form NMR (CDCl$_3$): 7.14 (s, 2H, Pyridazin-H); 5.78 (d, 1H, H$_{14}$, J$_{H14H13}$=8 Hz); 4.1 (s, 2H, S-CH$_2$-CO); 3.4 (m, 3H, H$_{11}$ und CH$_2$-N>); 2.9 (m, 2H, CH$_2$-S-); 2.66 (q, 4H, N-CH$_2$-CH$_3$); 1.1 (t, 6H, N-CH$_2$-CH$_3$); 1.46 (s, 3H,(CH$_3$)$_{15}$); 1.1 (s, 3H (CH$_3$)$_{18}$).

IR (KBr): 3400 (broad, OH), 1720 (CO), 1140 cm$^{-1}$.

EXAMPLE 19

14-O-[(4-Amino-1,2,4-triazol-3yl)thioacetyl]mutilin

NMR (CDCl$_3$): 8.26 (s, 1H, Triazol-H); 5.7 (d, 1H, H$_{14}$, J$_{H14H13}$=8 Hz); 5,08 (s 2H,NH$_2$), AB-System ($v_A$=3.86, $v_B$=3.75, J$_{AB}$=16.2 Hz, S-CH$_2$-O); 3,34 (dd, 1H, H$_{11}$, J=6.3 Hz, J=10.2 Hz).

IR (KBr): 3400 (broad), 1720 cm$^{-1}$.

EXAMPLE 20

14-O-[(3-(4-Pyridyl)-1,2,4-triazol-5-yl)thioacetyl]-mutilinhydrochlorid

NMR (DMSO): 8.95 (d, 2H, Pyridin-H, J=6.3 Hz); 8.36 (d, 2H-Pyridin-H, J=6.3 Hz); 5.55 (d, 1H, H$_{14}$, J$_{H14H13}$=8 Hz); 4.16 (s, 2H, S-CH$_2$-CO); 3.4 (d, 1H, H$_{11}$, J$_{H10H11}$=6.3 Hz).

IR (KBr): 3600–2500 (broad), 1725, 1635 cm$^{-1}$.

EXAMPLE 21

14-O-[(4-Amino-3-trifluormethyl-1,2,4-triazol-5-yl)thioacetyl]mutilin

NMR (CDCl$_3$): 5.74 (d, 1H, H$_{14}$, J$_{H14H13}$=8 Hz); 5.18 (s, 2H, NH$_2$); 3.9 (s, 2H, S-CH$_2$CO); 3.38 (m, 1H, H$_{11}$).

IR (KBr): 3400 (broad), 1720, 1190, 1150 cm$^{-1}$.

EXAMPLE 22

14-O-[(4-Amino-3-methyl-1,2,4-triazol-5-yl)thioacetyl]-mutilin

NMR (CDCl$_3$): 5.72 (d, 1H, H$_{14}$, J$_{H14H13}$=8 Hz); 4.97 (s, 2H, NH$_2$); AB-System ($v_A$=3.84, $v_B$=3.69, J$_{AB}$=16.2 Hz, S-CH$_2$-CO); 3.38 (dd, H$_{11}$, J=6.3 Hz, J=10.2 Hz).

IR (KBr): 3400 (broad), 1725 cm$^{-1}$.

EXAMPLE 23

14-O-[(3-Methyl-4-acetamido-1,2,4-triazol-5-yl)thioacetyl]mutilin

NMR (CDCl$_3$): 5.7 (d, 1H, H$_{14}$, J$_{H14H13}$=8 Hz); 3.8 (s, 2H, S-CH$_2$-CO); 3.38 (m, 1H, H$_{11}$); 2.33 (s, 3H, CH$_3$CO-N); 2.26 (s, 3H, Triazol-CH$_3$).

IR (KBr): 3400 (broad), 1720, 750 cm$^{-1}$.

EXAMPLE 24

14-O[(3-(Methoxysulfonylethylcarboxamido)-1,2,4-triazol-5-yl)thioacetyl]mutilin

NMR (CDCl$_3$): 5.72 (d, 1H, H$_{14}$, J$_{H14H13}$=8 Hz); 3.82 (s, 2H, S-CH$_2$-CO); 3.34 (m, 1H, H$_{11}$); 3.14 (s, 3H, -O-CH$_3$).

IR (KBr): 3400 (broad), 1720, 1625, 1550, 1305, 1110, 730 cm$^{-1}$.

EXAMPLE 25

14-O-[(4-Ethylaminocarbonyl-3-amino-1,2,4-triazol-5-yl)thioacetyl]mutilin

NMR (CDCl$_3$/CD$_3$OD 10:1): 5.74 (d, 1H, H$_{14}$, J$_{H14H13}$=8 Hz); 3.75 (s, 2H, S-CH$_2$-CO); 3.38 (q, 2H, CH$_3$-CH$_2$-N); 3.4 (m, 1H, H$_{11}$); 1.26 (t, 3H, $\underline{CH_3}$-$\overline{CH_2}$-N).

IR (KBr): 3540, 3430, 3310, 1710, 1630, 1300 cm$^{-1}$.

m.p.: 230°–232°.

EXAMPLE 26

14-O-[(3-Amino-4-formyl-1,2,4-triazol-5-yl)thioacetyl]-mutilin

NMR (CDCl$_3$): 8.52 (s, 1H, Formyl-H); 5.74 (d, 1H, H$_{14}$, J$_{H14H13}$=8 Hz); 3.82 (s, 2H, S-CH$_2$CO); 3.36 (m, 1H, H$_{11}$).

IR (KBr): 3600–2800 (broad), 1725, 1585, 1290 cm$^{-1}$.

EXAMPLE 27

14-O-{[3-Amino-4-(carbethoxythiocarbamyl)-1,2,4-triazol-5-yl]thioacetyl}mutilin

NMR (CDCl$_3$): 7.74 (b, 2H, NH$_2$); 5.81 (d, 1H, H$_{14}$, J$_{H14H13}$=8 Hz); 4.37 (q, 2H, O-CH$_2$CH$_3$); 3.83 (s, 2H, S-CH$_2$-CO); 3.4 (d, 1H, H$_{11}$, J$_{H11H10}$=6.3 Hz); 1.38 (t, 3H, O-CH$_2$CH$_3$).

IR (KBr): 3300 (broad), 1770, 1725, 1635, 1465, 1185 cm$^{-1}$.

EXAMPLE 28

14-O-[(3-Amino-4-(Ethylaminothiocarbonyl)-1,2,4-triazol-5-yl)thioacetyl]mutilin

NMR (CDCl$_3$): 8.56 (m, 1H, NH); 7.4 (b, 2H, NH$_2$); 5.76 (d, 1H, H$_{14}$, J$_{H14H13}$=8 Hz); 3.78 (s, 2H, S-CH$_2$-CO); 3.68 (m, 2H, N-CH$_2$-CH$_3$); 3.38 (dd, 1H, H$_{11}$, J=6.3 Hz, J=10.2 Hz); 1.33 (t, 3H, N-CH$_2$-CH$_3$).

IR (KBr): 3340 (broad), 1720, 1630, 1290 cm$^{-1}$.

EXAMPLE 29

14-O-{[4-Bis-(methylsulfonyl)amino-1,2,4-triazol-3-yl]thioacetyl}mutilin

NMR (CDCl$_3$): 8.28 (s, 1H, Triazol-H); 5.72 (d, 1H, H$_{14}$, J$_{H14H13}$=8 Hz); AB-System (v$_A$=4.18, v$_B$=4.02, J$_{AB}$=16.2 Hz, S-CH$_2$-CO); 3.6 (s, 3H, CH$_3$SO$_2$—); 3.58 (s, 3H, CH$_3$SO$_2$—); 3.34 (m, 1H, H$_{11}$).

IR (KBr): 3450 (broad), 1720, 1380, 1160 cm$^{-1}$.

EXAMPLE 30

14-O-[(Benzimidazol-2-yl-methyl)thioacetyl]mutilinhydrochloride

NMR (CDCl$_3$): 7.6 (m, 2H, arom. H); 7.2 (m, 2H, arom. H); 5.8 (d, 1H, H$_{14}$, J$_{H14H13}$=8 Hz); 4.07 (s, 2H, S-CH$_2$-arom.); 3.42 (m, 1H, H$_{11}$); 3.25 (s, 2H, S-CH$_2$-CO).

IR (KBr): 3600–2700 (broad), 1720, 1270, 740 cm$^{-1}$.

EXAMPLE 31

14-O-[(2-Methyl-4-hydroxypyrimidin-6-yl)methylthioacetyl]mutilin

NMR (CDCl$_3$): 6.3 (s, 1H, NH); 5.74 (d, 1H, H$_{14}$, J$_{H14H13}$=8 Hz); 3.58 (s, 2H, S-CH$_2$-Arom.); 3.36 (m, 1H, H$_{11}$), 3.14 (s, 2H, S-CH$_2$-CO); 2.46 (s, 3H, Pyrimidin-CH$_3$).

IR (KBr): 3400 (broad), 1720, 1650, 1590, 1270, 1110 cm$^{-1}$.

EXAMPLE 32

19,20-Dihydro-14-O-[(3-diethylaminoethylthiopyridazin-6-yl)thioacetyl]mutilin, fumarate form NMR (CDCl$_3$): 7.14 (s, 2H, Pyridazin-H); 6.78 (s, 1H, fumaric acid-H); 5.6 (d, 1H, H$_{14}$, J$_{H14H13}$=8 Hz); AB-System (v$_A$=4.14, v$_B$=3.92, J$_{AB}$=16.2 Hz); 2.97 (q, 4H, N-CH$_2$-CH$_3$); 1.23 (t, 6H, N-CH$_2$-CH$_3$); 3.6–3.1 (m, 4H, S-CH$_2$-CH$_2$-N<).

IR (KBr): 3400 (broad), 1720, 1385, 1140, 1110 cm$^{-1}$.

EXAMPLE 33

14-O-{[3-(2-Pyridyl)-1,2,4-triazol-5-yl]thioacetyl}mutilin

NMR (CDCl$_3$): 8.82 (d, 1H, Pyridin-H, J=5 Hz); 8.24 (d, 1H, Pyridin-H, J=10 Hz); 7.9 (m, 1H, Pyridin-H); 7.45 (m, 1H, Pyridin-H); 5.78 (d, 1H, H$_{14}$, J$_{H14H13}$=8 Hz); 4.0 (s, 2H, S-CH$_2$-CO); 3.4 (m, 1H, H$_{11}$).

IR (KBr): 3500–2800 (broad), 1720, 1450, 1280 cm$^{-1}$.
UV (CH$_3$OH): 232 nm (ε=12400), 282 (8170).

EXAMPLE 34

14-O-[(2-Methyl-1,3,4-thiadiazol-5-yl)thioacetyl]mutilin

NMR (CDCl$_3$): 5.78 (d, 1H, H$_{14}$, J$_{H14H13}$=8.1 Hz); 4.07 (s, 2H, CH$_2$-S-CO); 3.38 (dd, 1H, H$_{11}$, J$_{H11H10}$=6.3 Hz, J$_{H11OH}$=10,8 Hz); 2.72 (s, 3H, CH$_3$-thiadiazol).

IR (KBr): 3400 (OH)(broad) 1730 (CO) cm$^{-1}$.
UV (CH$_3$OH): 264 nm (ε=5330).

EXAMPLE 35

14-O[(2-Amino-1,3,4-thiadiazol-5-yl)thioacetyl]mutilin

NMR (CDCl$_3$): 5.74 (d, 1H, H$_{14}$, J$_{H14H13}$=8.1 Hz); 5.32 (b, 2H, NH$_2$); 3.88 (s, 2H, S-CH$_2$-CO); 3.34 (m, 1H, H$_{11}$).

IR (KBr): 3400 (NH$_2$, OH); 1730 (CO) cm$^{-1}$.
UV (CH$_3$OH): 282 nm (ε=7150).

What is claimed is:
1. A compound of the formula

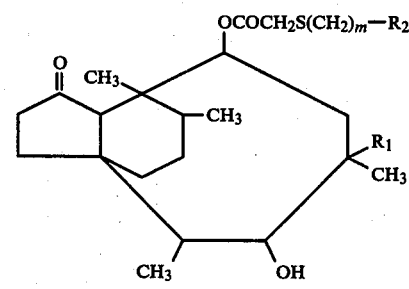

in which
R$_1$ is ethyl or vinyl,
m is 0 or 1, and
R$_2$ is

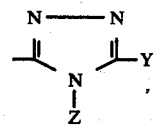

in which
Z is hydrogen, lower alkylsulphonyl, amino, formyl,

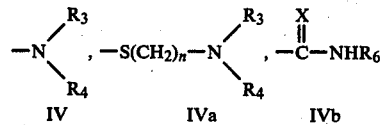

in which
either R$_3$ and R$_4$ are the same or different and each is hydrogen, lower hydroxyalkyl, lower dihydroxyalkyl, unsubstituted or lower alkoxysulphonyl substituted lower alkanoyl, lower alkyl sulphonyl or lower alkyl,
or R$_3$ and R$_4$ together with the nitrogen atom form a piperazinyl radical, which may be substituted on the second nitrogen atom by lower alkyl, lower hydroxyalkyl or lower dihydroxyalkyl,
n is 2 to 5,
X is oxygen or sulphur, and
$R_6$ is lower alkyl or lower alkoxycarbonyl, and
Y is hydrogen, amino, trifluoromethyl, lower alkyl, pyridyl or

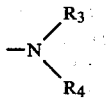

where $R_3$ and $R_4$ are as defined above, or a chemotherapeutically acceptable acid addition or quaternary ammonium salt thereof.

2. The compound of claim 1, which is 19,20-dihydro-14-O-[(3-amino-1,2,4-triazol-5-yl)thioacetyl]mutilin.

3. The compound of claim 1 which is 14-O-[3-amino-1,2,4-triazol-5-yl)thioacetyl]mutilin.

4. The compound of claim 1 which is 14-O-[(4-methylsulfonyl-5-amino-1,2,4-triazole-3-yl)thioacetyl]mutilin.

5. The compound of claim 1 which is 14-O-[(4-amino-1,2,4-triazol-3-yl)thioacetyl]mutilin.

6. The compound of claim 1 which is 14-O-[(3-(4-pyridyl)-1,2,4-triazol-5-yl)thioacetyl]mutilin hydrochloride.

7. The compound of claim 1 which is 14-O-[(4-amino-3-trifluoromethyl-1,2,4-triazol-5-yl)thioacetyl]mutilin.

8. The compound of claim 1 which is 14-O-[(4-amino-3-methyl-1,2,4-triazol-5-yl)thioacetyl]mutilin.

9. The compound of claim 1 which is 14-O-[(3-methyl-4-acetamido-1,2,4-triazol-5-yl)thioacetyl]mutilin.

10. The compound of claim 1 which is 14-O[(3-methoxysulfonylethylcarboxamido)-1,2,4-triazol-5-yl)thioacetyl]mutilin.

11. The compound of claim 1 which is 14-O-[(4-ethylaminocarbonyl-3-amino-1,2,4-triazol-5-yl)thioacetyl]mutilin.

12. The compound of claim 1 which is 14-O-[(3-amino-4-formyl-1,2,4-triazol-5-yl)thioacetyl]mutilin.

13. The compound of claim 1 which is 14-O-[[(3-amino-4-(carbethoxythiocarbamyl)-1,2,4-triazol-5-yl]thioacetyl]mutilin.

14. The compound of claim 1 which is 14-O-[(3-amino-4-(ethylaminothiocarbonyl)-1,2,4-triazol-5-yl)thioacetyl]mutilin.

15. The compound of claim 1 which is 14-O-[[4-bis(-methylsulfonyl)amino-1,2,4-triazol-3-yl]thioacetyl]-mutilin.

16. The compound of claim 1 which is 14-O-[[3-(2-pyridyl)-1,2,4-triazol-5-yl]thioacetyl]mutilin.

17. A method of treating microbial infections comprising administering to a subject in need of such treatment, a chemotherapeutically effective amount of a compound of claim 1.

18. A composition useful in treating microbial infections comprising an antimicrobial effective amount of a compound of claim 1, in association with an antimicrobial acceptable diluent or carrier.

* * * * *